United States Patent
Liu et al.

(10) Patent No.: US 11,117,132 B2
(45) Date of Patent: Sep. 14, 2021

(54) BIOCOMPATIBLE MICROPILLAR ARRAY SUBSTRATE AND METHODS FOR FABRICATING SUCH SUBSTRATE

(71) Applicant: Lian Liu, Tarzana, CA (US)

(72) Inventors: Lian Liu, Tarzana, CA (US); Shuang Hou, Westlake Village, CA (US); Chun-Hao Luo, Agoura Hills, CA (US)

(73) Assignee: Lian Liu, Tarzana, CA (US)

( * ) Notice: Subject to any disclaimer, the term of this patent is extended or adjusted under 35 U.S.C. 154(b) by 0 days.

(21) Appl. No.: 16/401,991

(22) Filed: May 2, 2019

(65) Prior Publication Data

US 2020/0009567 A1 Jan. 9, 2020

Related U.S. Application Data

(63) Continuation of application No. 16/282,640, filed on Feb. 22, 2019.

(60) Provisional application No. 62/694,941, filed on Jul. 6, 2018, provisional application No. 62/694,944, filed on Jul. 6, 2018, provisional application No. 62/694,945, filed on Jul. 6, 2018.

(51) Int. Cl.
| | |
|---|---|
| *B01L 3/00* | (2006.01) |
| *B01L 1/00* | (2006.01) |
| *A61B 5/15* | (2006.01) |
| *C12N 5/09* | (2010.01) |
| *G01N 33/50* | (2006.01) |

(52) U.S. Cl.
CPC ...... *B01L 3/502761* (2013.01); *A61B 5/1405* (2013.01); *C12N 5/0693* (2013.01); *G01N 33/5094* (2013.01); *B01L 2200/0668* (2013.01); *B01L 2300/088* (2013.01); *B01L 2300/0822* (2013.01); *B01L 2300/0848* (2013.01); *B01L 2300/0864* (2013.01); *B01L 2300/0874* (2013.01); *B01L 2300/12* (2013.01)

(58) Field of Classification Search
CPC ......... B01L 2300/0874; B01L 2300/12; B01L 3/502761
See application file for complete search history.

(56) References Cited

U.S. PATENT DOCUMENTS

| | | | |
|---|---|---|---|
| 2003/0148401 A1* | 8/2003 | Agrawal | B81C 1/00206 506/9 |
| 2005/0273995 A1* | 12/2005 | Kanagasabapathi | B03C 5/026 29/592.1 |
| 2009/0018033 A1* | 1/2009 | Morgan | C12N 5/0012 506/26 |
| 2011/0160869 A1* | 6/2011 | Duch | C12M 25/06 623/23.5 |
| 2015/0368599 A1* | 12/2015 | Maher | C12M 23/12 435/305.2 |
| 2016/0202123 A1* | 7/2016 | Jung | C23C 14/04 359/327 |
| 2016/0214107 A1* | 7/2016 | Viasnoff | G01N 21/03 |

(Continued)

*Primary Examiner* — Nathan A Bowers

(57) ABSTRACT

A biocompatible micropillar array substrate (MAS) and methods for preparing the biocompatible MAS are provided. In on example, the biocompatible MAS includes multiple micropillars made from a biocompatible polymer. The biocompatible MAS may be prepared using a replica fabricated based on a silicon MAS. The configuration of the multiple micropillars of the silicon MAS and a configuration of the multiple micropillars of the biocompatible MAS are the same.

13 Claims, 8 Drawing Sheets

(56) References Cited

U.S. PATENT DOCUMENTS

2017/0038285 A1\* 2/2017 Zheng .................. G01N 33/552
2018/0066299 A1\* 3/2018 Kim ................... G01N 33/5002

\* cited by examiner

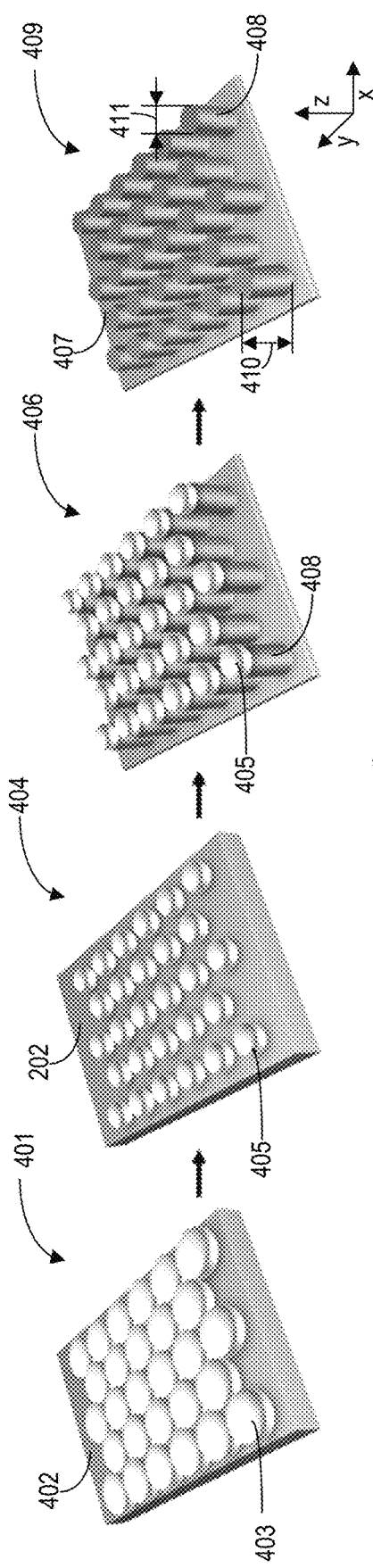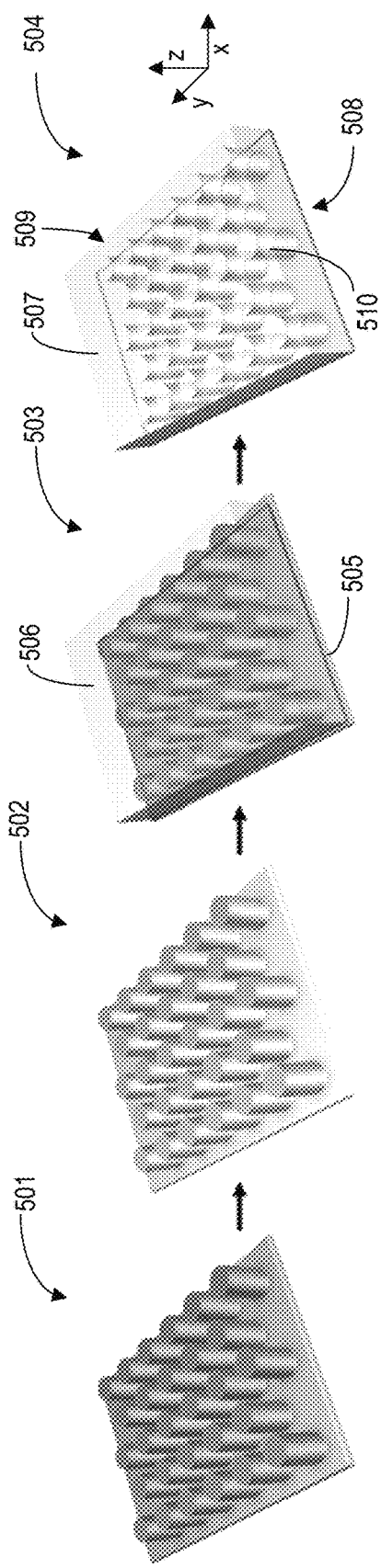

BIOCOMPATIBLE MICROPILLAR ARRAY SUBSTRATE AND METHODS FOR FABRICATING SUCH SUBSTRATE

CROSS REFERENCE TO RELATED APPLICATIONS

The present application is a continuation application of U.S. Non-Provisional application Ser. No. 16/282,640, filed on Feb. 22, 2019.

The present application claims priority to 1) U.S. Provisional Patent Application Ser. No. 62/594,941, entitled "A Method and Device for CTC Capture and Characterization", filed on Jul. 6, 2018, 2) U.S. Provisional Patent Application Ser. No. 62/694,944, entitled "Non-Invasive Prenatal Test on Single Fetal Cells Isolated from Blood of Pregnant Women", filed on Jul. 6, 2018, 3) U.S. Provisional Patent Application Ser. No. 62/694,945, entitled "Simple and Eco-Friendly Fabrication of Biocompatible Micropillar Array Substrate (MAS) Using Micro-Imprinting", filed on Jul. 6, 2018, and 4) U.S. Non-Provisional application Ser. No. 16/282,640, filed on Feb. 22, 2019. The entire contents of the above-identified applications are incorporated herein by reference for all purposes.

FIELD

The present description relates generally to biocompatible micropillar array substrate, and more specifically to biocompatible micropillar array substrate to simulate the microenvironment around cells.

BACKGROUND

Cells reside and survive in a complex microenvironment of extracellular matrix (ECM). The ECM plays an important role in cell morphology and function. The ECM contains structures in the micron or submicron scales. Structures in the same scale of the ECM may be used to study cell attachment, proliferation, and evolution. For example, a micropillar array substrate including micropillars in the micron scale may be used to study cell adhesion.

SUMMARY

In one embodiment, a method for preparing a biocompatible micropillar array substrate (MAS) with multiple micropillars comprises preparing a replica based on a silicon MAS with multiple micropillars, and preparing the biocompatible MAS by imprinting the replica on a layer of biocompatible polymer, where a configuration of the multiple micropillars of the silicon MAS and a configuration of the multiple micropillars of the biocompatible MAS are the same.

In another embodiment, a biocompatible micropillar array substrate comprises a plurality of micropillars of a biocompatible polymer arranged on a surface of a flat substrate, the plurality of micropillars spaced less than 10 µm from each other and having a height of 10 µm or less, the biocompatible MAS prepared based on a silicon MAS with a plurality of micropillars, wherein a configuration of the plurality of micropillars of the silicon MAS and a configuration of the plurality of micropillars of the biocompatible MAS are the same.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 4 schematically illustrates an example method for fabricating a silicon MAS.

FIG. 5 schematically illustrates an example process for fabricating a polydimethylsiloxane (PDMS) replica using the silicon MAS of FIG. 4.

DETAILED DESCRIPTION

The following description relates to a biocompatible micropillar array substrate (MAS) and methods for manufacturing the biocompatible MAS. The biocompatible MAS may include multiple micropillars over a flat substrate. The biocompatible MAS may simulate different mechanical properties of the extracellular matrix (ECM) affecting the cell proliferation or cell attachment. The micropillars on the biocompatible MAS are in the micron or submicron scale to simulate the dimension of the ECM. The micropillars need to be accurately fabricated in high resolution, as the cells are sensitive to the size of the micropillars. Further, the biocompatible MAS needs to have a large and accessible surface area to facilitate applications such as cell sorting. Colloidal lithography techniques, compared to the other generally used photolithography with photo mask, may be used to generate micropillar arrays that meet the above criteria. Colloidal lithography techniques include microbeads that are utilized to form a uniform template for further control of micropillar dimension. Subsequent lithographic processing of colloidal substrates utilizing, for example, reactive ion etching allows the production of modified colloidal-derived micropillar array substrates. However, the instrument(s) used in this process is not very often equipped in a regular chemistry lab, and thus fabrication of micropillar arrays may be expensive and/or difficult to customize for a particular use. Therefore, embodiments disclosed herein use eco-friendly wet etching technique to address this issue.

Figure 1:
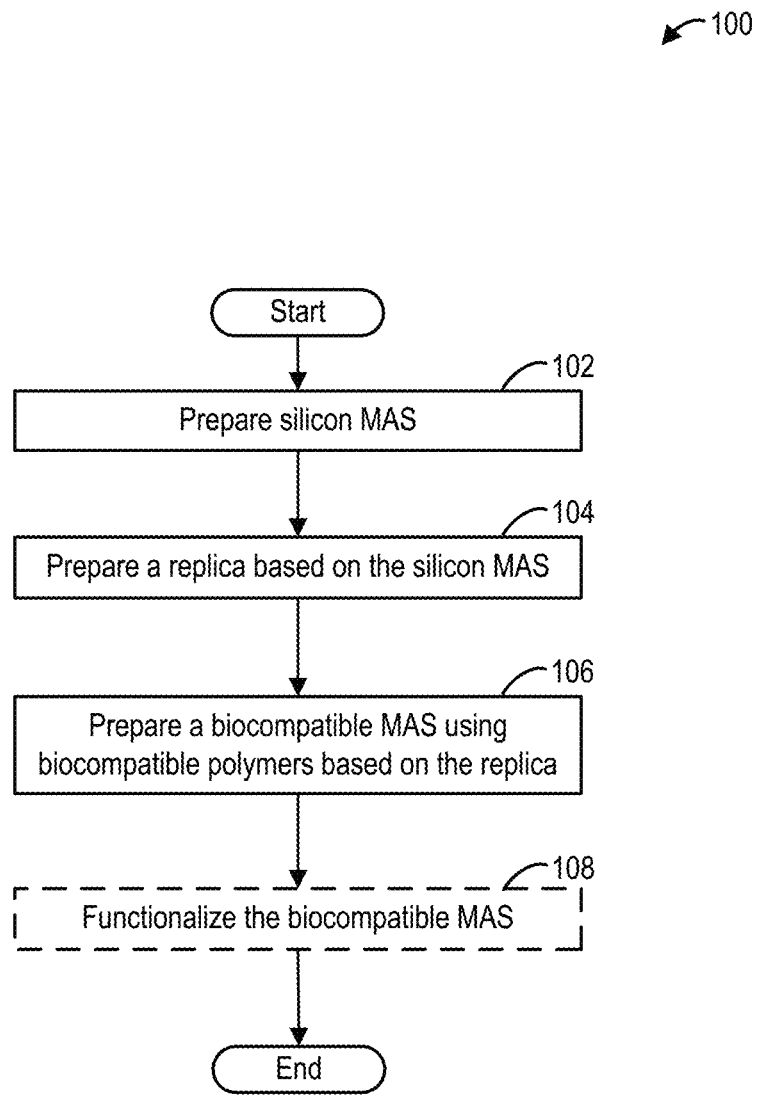
FIG. 1 is a top level flow chart for preparing a biocompatible micropillar array substrate (MAS).
Figure 2:
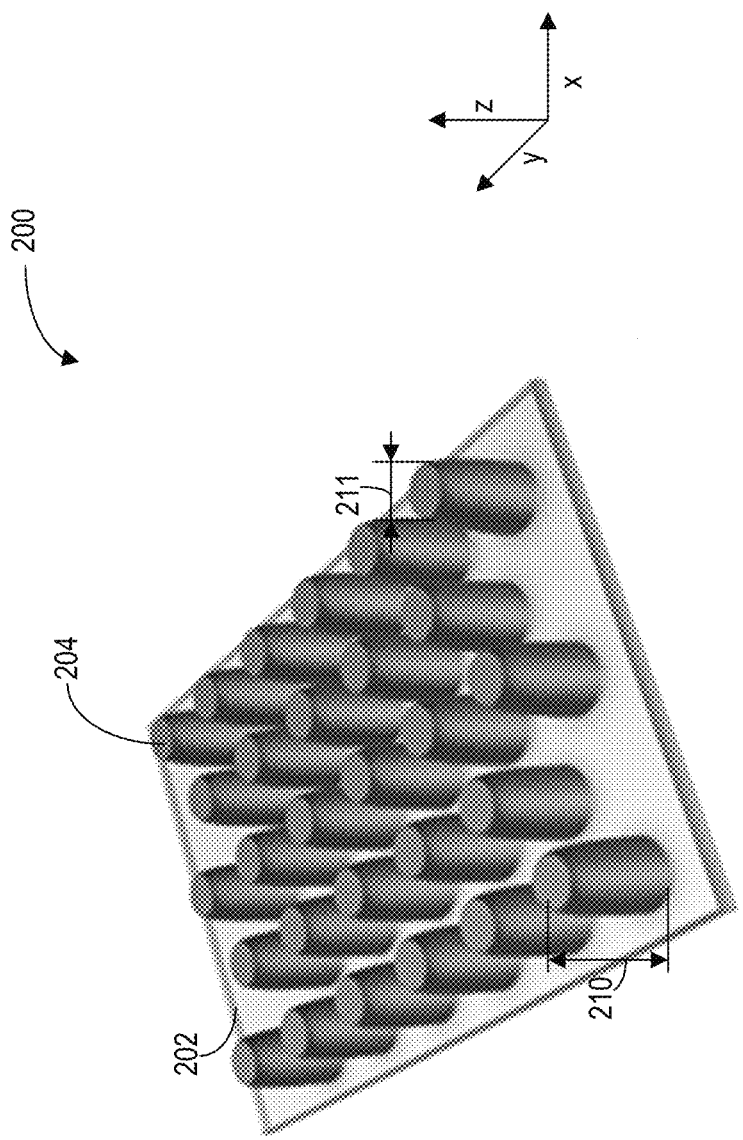
FIG. 2 shows an example configuration of micropillars of the MAS.
Figure 3:
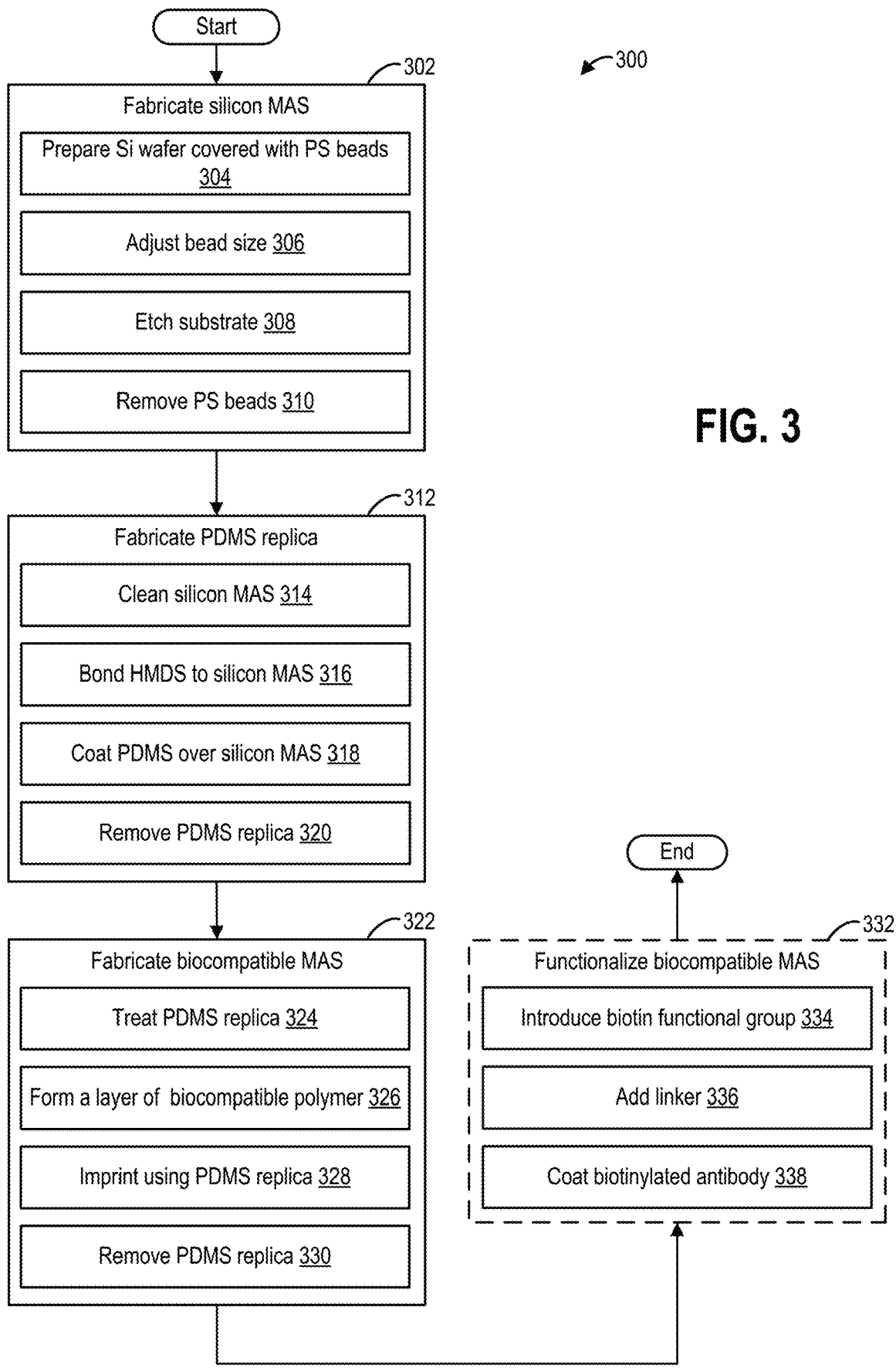
FIG. 3 shows an example method for fabricating the biocompatible MAS, according to some embodiments.
Figure 6:
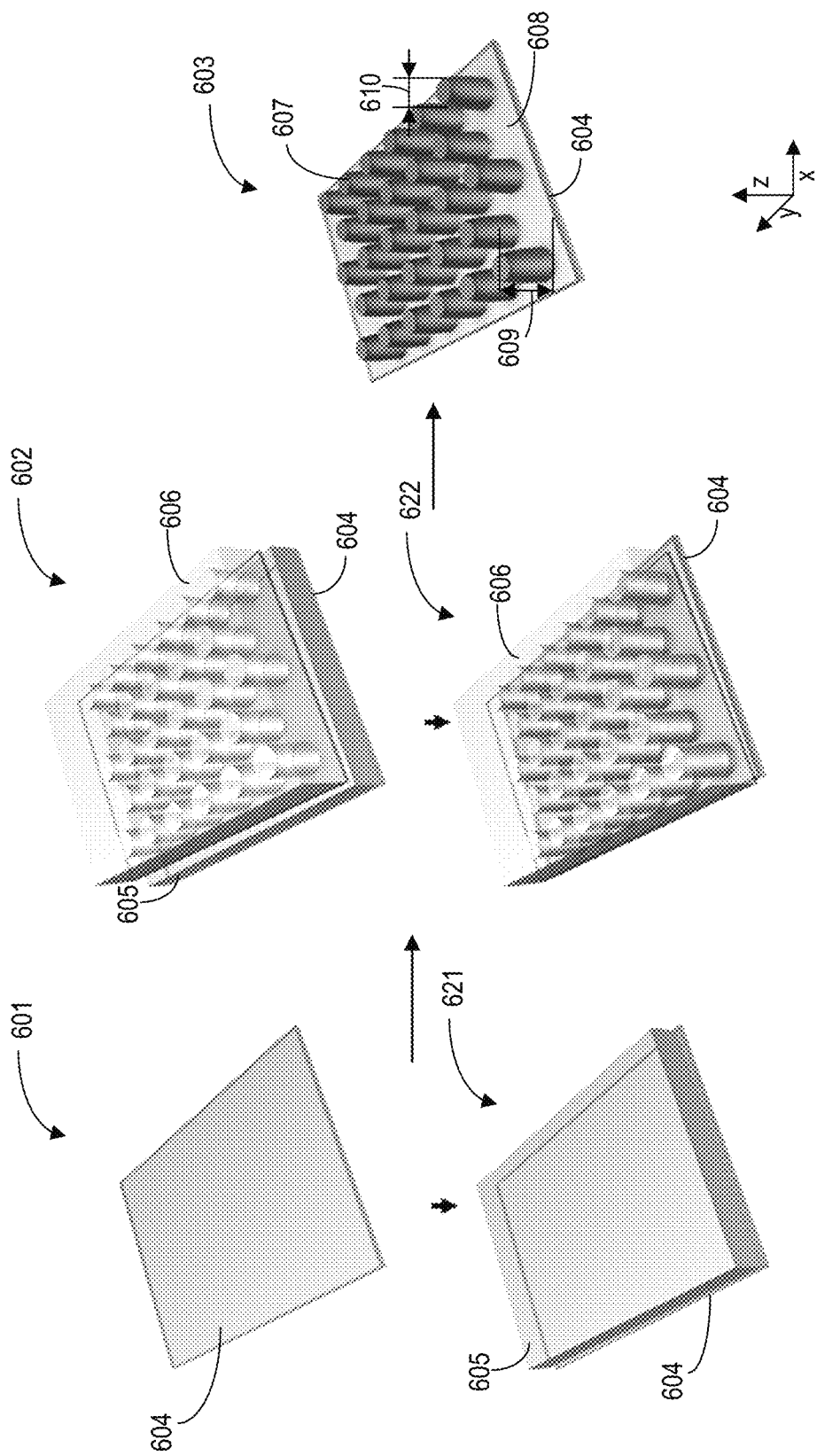
FIG. 6 schematically illustrates an example process for fabricating a biocompatible MAS using the PDMS replica of FIG. 5.
Figure 7:
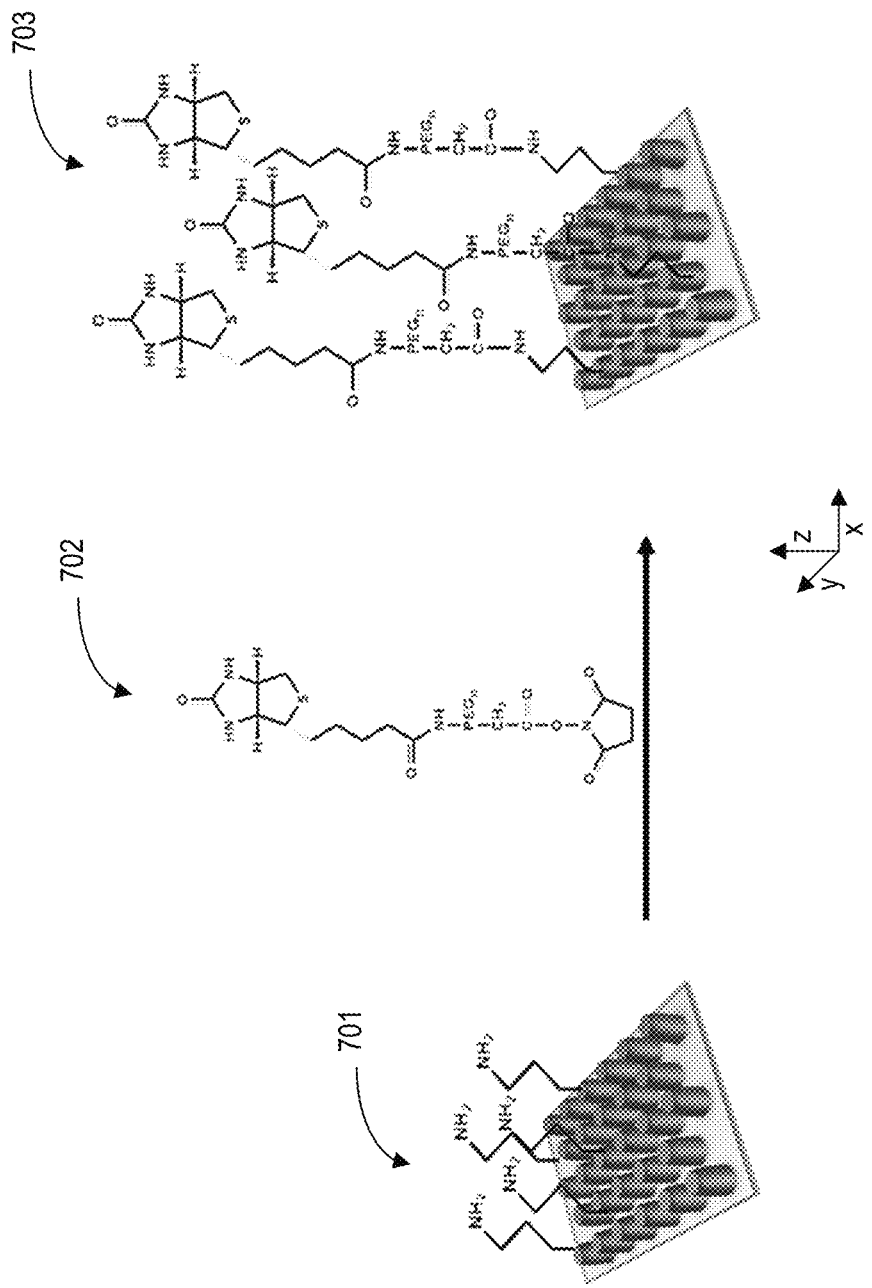
FIG. 7 schematically illustrates an example process for functionalizing the biocompatible MAS of FIG. 6.
Figure 8:
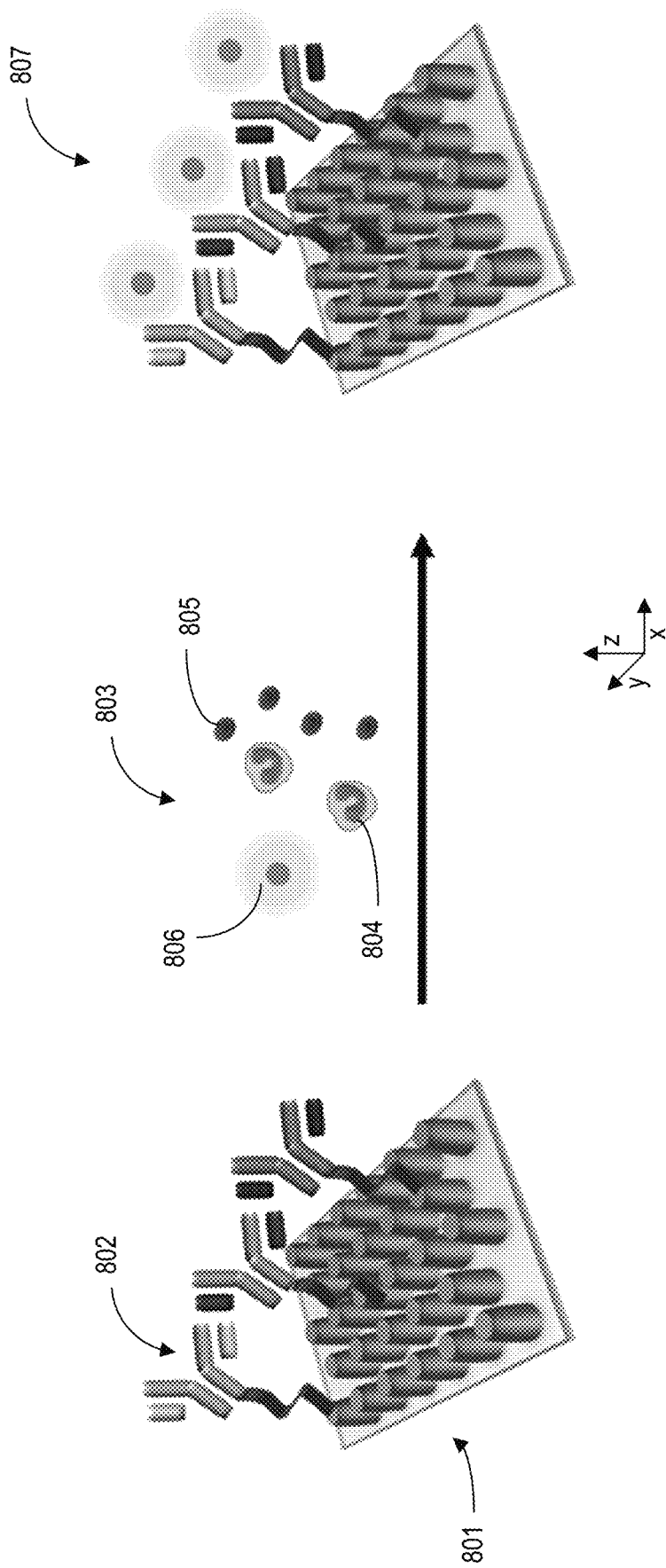
FIG. 8 illustrates an example process of selective cell adhesion using the functionalized biocompatible MAS of FIG. 7.
Figure 9:
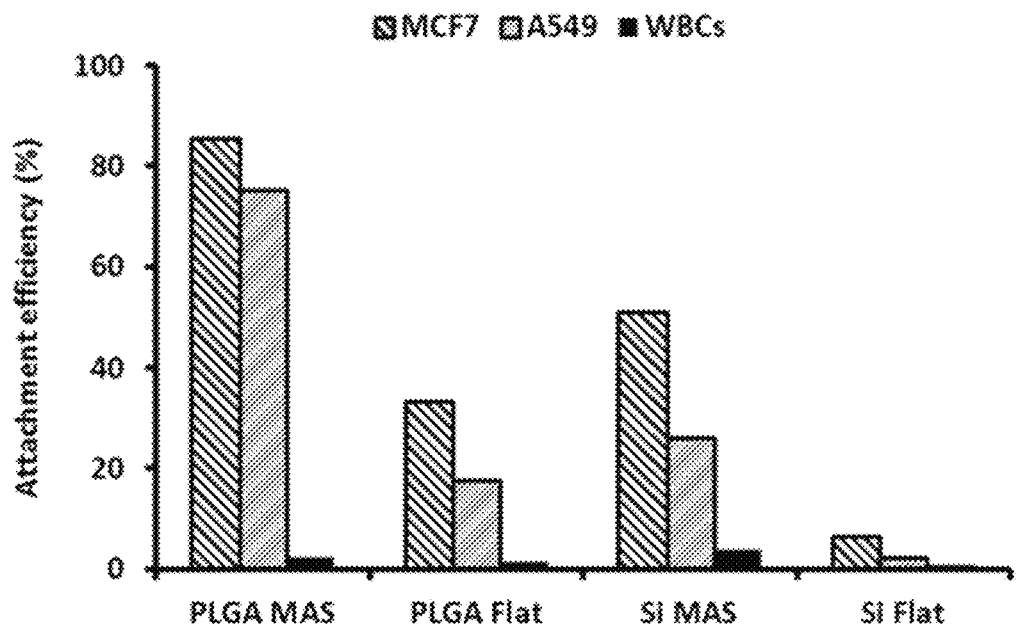
FIG. 9 is a figure showing cell attachment efficiency of various substrates.
Figure 10:
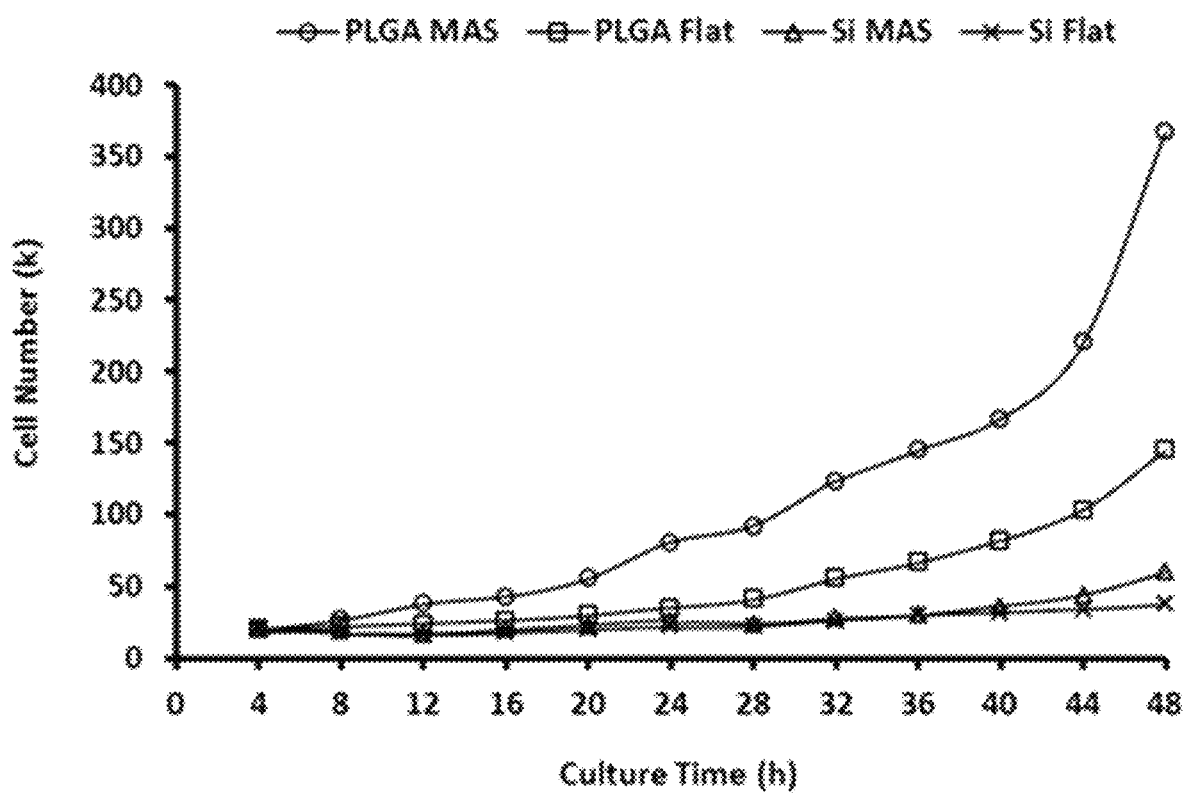
FIG. 10 is a figure showing cell proliferation on various substrates.

FIG. 1 shows a top level flow chart for preparing a biocompatible MAS. The biocompatible MAS may be obtained by imprinting a replica onto a layer of biocompatible polymer. The replica may be made based on a silicon MAS. The biocompatible MAS and the silicon MAS may have the same configuration of micropillars. FIG. 2 shows an example configuration of micropillars of the MAS. In some embodiments, the replica may be made out of polydimethylsiloxane (PDMS). FIG. 3 shows an example method for manufacturing the biocompatible MAS using the PDMS replica. In particular, the PDMS replica may be fabricated using a master mold of silicon MAS produced via eco-friendly wet etching technique. The biocompatible MAS may further be functionalized with antibodies to selectively increase the cell adherence efficiency. FIG. 4 illustrates the process of fabricating the silicon MAS with colloid lithography. FIG. 5 illustrates the process of manufacturing the PDMS replica from the silicon MAS. FIG. 6 illustrates the process of imprinting the PDMS replica onto a biocompatible polymer coated substrate to obtain the biocompatible MAS. FIG. 7 illustrates the process of functionalizing the biocompatible MAS with biotinylated antibody. FIG. 8 illustrates selective cell adhesion of the functionalized biocompatible MAS. FIG. 9 and FIG. 10 show that the biocompatible MAS may increase cell attachment efficiency and cell proliferation comparing to other types of substrates.

Turning to FIG. 1, a top-level schematic 100 for preparing a biocompatible MAS is shown. The biocompatible MAS may be fabricated based on a silicon MAS. The configuration of micropillars in the silicon MAS is duplicated to the biocompatible MAS using a replica.

At 102, the silicon MAS is prepared. In some embodiments, the silicon MAS may be fabricated with a photolithography process. In some embodiments, the silicon MAS may be fabricated via an eco-friendly colloid lithography process. Comparing to the photolithography process, the eco-friendly colloid lithography process does not require print-out mask and mask alignment equipment, and therefore may be easily implemented to reproduce micropillars with high precision.

An example micropillar configuration of a silicon MAS 200 is shown in FIG. 2. The MAS may include multiple micropillars 204 arranged on one side of a flat substrate 202. Herein, the micropillar configuration includes the size, dimension, and shape of the micropillars, as well as the position and the arrangement of the micropillars on the flat substrate. The flat substrate may extend in the x-y plane. The micropillars may extend in the z direction. The height of the micropillar is measured in the z direction, and the height increases as indicated by the arrow of z-axis. In some embodiments, the micropillars may be the same size (e.g., height, shape, and thickness are the same). For example, the height 210 of each micropillar may be 10 μm or less. In one example, the height of the micropillar is 5-10 μm. In another example, the height of the micropillars may be 2 μm. The spacing of the micropillars may be 10 μm or less. That is, the distance between adjacent micropillars may be 10 μm or less. In one example, the micropillars are 10 μm away from each other. In another example, the micropillars are 2 μm or less away from each other, such as 0.2-2 μm from a center of one micropillar to a center of a neighboring micropillar. In some embodiments, each micropillar may be cylindrical in shape. The diameter 211 in a lateral cross-section (the cross-section parallel to the flat substrate 202) of the micropillar may be less than 2 μm, at least in some examples. In one example, the diameter 211 is 0.8-2 μm. In some embodiments, each micropillar may be a cylindrical cone. The diameter of the lateral cross-section of the cylindrical cone may decrease with increased height. In one example, the diameter of the lateral cross-section is equal to or less than 2 μm. In other examples, the micropillars may vary in height, shape, and thickness. In some examples, the height, shape, thickness, and/or spacing of the micropillars may be selected based on a target cell type (e.g., for selective cell adhesion) or other property.

Turning back to FIG. 1, at 104, a replica is prepared based on the silicon MAS. In particular, the silicon MAS may serve as a master mold used for molding one or more replicas that are complimentary to the silicon MAS. The replica(s) may include multiple indentations, and each indentation may be complimentary to a micropillar (such as micropillar 204 of FIG. 2) of the silicon MAS.

At 106, a biocompatible MAS having the same micropillar configuration as, but different material from, the silicon MAS is prepared with the replica. In other words, the biocompatible MAS mirrors the silicon MAS. In some embodiments, a biocompatible material may flow into and fill the indentations of the replica, and form micropillars of the biocompatible MAS. In some embodiments, the replica may imprint on a layer of viscous biocompatible material, such as a biocompatible polymer, to form the biocompatible MAS. The biocompatible micropillar arrays may then be solidified and removed from the replica to obtain the biocompatible MAS.

At 108, the biocompatible MAS may optionally be functionalized with an antibody targeting one or multiple cell types.

In this way, the biocompatible MAS having the same configuration of micropillars (such as the configuration of micropillars shown in FIG. 2) as the silicon MAS is manufactured. In other words, the size and distribution of the micropillars of the biocompatible MAS are the same as the silicon MAS. In some embodiments, the replica may be reused for fabricating multiple biocompatible MAS. Alternatively, in some embodiments, multiple replicas may be used simultaneously for fabricating a biocompatible MAS covering a large surface area. For example, multiple replicas may be arranged side by side on the biocompatible polymer coated substrate to fabricate the biocompatible MAS.

FIG. 3 is a flow chart showing an example method 300 for fabricating a biocompatible MAS or a functionalized biocompatible MAS. In particular, a silicon MAS may first be fabricated using the eco-friendly colloid lithography process. A PDMS replica is then obtained using the silicon MAS as a master mold. By imprinting the PDMS replica onto a biocompatible polymer coated substrate, the biocompatible MAS may be fabricated. The biocompatible MAS may be further functionalized with antibodies to obtain the functionalized biocompatible MAS.

At 302, the silicon MAS is fabricated. The silicon MAS may be fabricated via an eco-friendly colloid lithography process. For example, the micropillar arrays are produced by wet etching the silicon substrate with polystyrene (PS) beads self-assembled on the surface of the silicon substrate.

Fabricating the silicon MAS includes, at 304, preparing the silicon wafer with PS beads dispersed on the surface. In one example, one surface of the silicon wafer is covered with a single layer of PS beads. The PS beads may be immobilized over the silicon wafer surface. In some embodiments, the silicon substrate may be thicker (e.g. greater) than 10 μm in the vertical direction, and the PS beads may be of a diameter from 2-10 μm.

In some embodiments, the PS beads may be self-assembled into a single layer. For example, the PS beads may be dissolved in ethanol to form a single layer and then transferred to the surface of a pre-cleaned silicon wafer. In one example, each of the PS beads in the single layer of PS bead is surrounded and in direct contact with six other PS beads. In one example, after air-dry and heating at 120° C.

for 2 minutes, the beads may be immobilized on the silicon wafer surface ready for plasma treatment.

Schematic 401 of FIG. 4 shows an example silicon substrate 402 with 2 μm spherical PS beads 403 dispersed on the top surface of the silicon substrate. The PS beads form a single layer fully covering the top surface of the silicon substrate. That is, except for the PS beads at the boundaries of the silicon substrate, each of the PS beads is surrounded, and in direct contact with a surrounding group of beads. In one example, as shown in the schematic 401, the surrounding group of beads include six PS beads. The location of the PS beads may determine the location of the micropillars. The size of the PS beads may determine distance between micropillars in the MAS. For example, biocompatible MAS fabricated with 2 μm diameter PS beads may result in micropillars spaced 2 μm from each other (that is, the central axis of the micropillars are 2 μm apart in the x-y plane).

Fabricating the silicon MAS includes, at 306, adjusting the size of the PS beads. In particular, the size of the PS beads may be reduced. The reduced diameter of the PS beads may determine the dimension of a lateral cross-section of the micropillars. In some embodiments, the diameter of the PS beads are reduced to 0.8-2 μm, or other suitable diameter.

In some embodiments, the size of the PS beads may be reduced by oxygen plasma treatment. For example, the silicon substrate with PS beads from 304 may be placed in a plasma chamber. Oxygen is introduced to the plasma chamber and interacts with the PS beads on the silicon substrate. The diameter of the PS beads are reduced after oxygen plasma treatment. The size of the PS beads may be adjusted to a diameter from 1 to 2 μm by adjusting the duration of the oxygen plasma treatment.

Schematic 402 of FIG. 4 shows the silicon substrate 402 with PS beads 405 dispersed on the surface of the substrate after the oxygen plasma treatment. The diameter of the PS beads 405 are smaller than the PS beads 403 in schematic 401.

Turning back to FIG. 3, fabricating the silicon MAS includes, at 308, etching the silicon substrate covered with PS beads to remove the silicon not covered by the PS beads. By removing the silicon not covered by the PS beads, but not the silicon directly under (or covered by) the PS beads, a micropillar is formed below (that is, lower in the vertical direction) each of the PS beads. The lateral cross-section of the micropillars may be not larger than the diameter of the PS bead on top of the micropillar.

In some embodiments, the silicon substrate covered with the reduced sized PS beads from 306 may be wet etched using $NH_4F$. The wet etching process may remove silicon of the silicon substrate that is not covered with the PS beads. In one example, the silicon substrate is first immersed in a first aqueous solution of silver nitrate ($AgNO_3$), $NH_4F$, and $H_2O_2$ for 15-30 minutes. The silicon substrate is then immersed in a second $NH_4F$ and $H_2O_2$ solution. By immersing the silicon substrate in the second $NH_4F$ and $H_2O_2$ solution without the $AgNO_3$, silicon nanowire structure in the silicon substrate may be removed.

Schematic 406 of FIG. 4 shows the etched silicon substrate with micropillars 408. The PS beads 405 are at the top of the micropillars. In other words, the micropillars are created at the same location in the x-y plane as the PS beads. The size of the PS beads 405 does not change after the etching procedure. The height of the micropillars 408 may be adjusted by adjusting the duration of immersing the silicon substrate in the first solution of $AgNO_3$, $NH_4F$, and $H_2O_2$. For example, the height of the silicon substrate may increase with increased immersion duration.

Turning back to FIG. 3, fabricating the silicon MAS includes, at 310, removing the PS beads from the silicon substrate to obtain the silicon MAS. In particular, the residual PS beads on top of each micropillar may be removed. In some embodiments, the PS beads may be removed by immersing the silicon substrate in acetone solvent under ultra-sonication for 5 minutes.

Schematic 409 of FIG. 4 shows the silicon MAS after removing the residual PS beads. The silicon MAS includes an array of identical silicon micropillars 408 protruding from a flat silicon bottom substrate. In some embodiments, each of the micropillars may be cylindrical. Alternatively, in some embodiments, each of the micropillars may be a cylindrical cone. The micropillars 408 and the flat bottom substrate 407 may be made from one silicon substrate 402. As such, the silicon MAS may be a piece of continuous material. The height 410 of each micropillars may be 10 μm or less, at least in some examples. In on example, the height of each micropillar is 5-10 μm, 1-5 μm, or other height, such as 2 μm. The diameter 411 of a lateral cross-section (the cross-section parallel to the flat bottom substrate 407) of the micropillar is less than 2 μm, at least in some examples. In one example, the diameter 411 is 0.8-2 μm. The distance between the micropillars may be under 2 μm. In one example, the micropillars are 0.2-1 μm away from each other. In other examples, the distance between the micropillars may be another suitable value, such as 2-5 μm.

Turning back to FIG. 3, at 312, a PDMS replica may be fabricated using the silicon MAS from 302. The surface of the silicon MAS may first be treated to prevent the silicon MAS from bonding to the PDMS. The replica may then be formed by coating PDMS over the treated silicon MAS. The PDMS replica may be removed from the silicon MAS after solidification. As such, the PDMS replica includes indentations that are of the same size and arrangement as the micropillars of the silicon MAS. The PDMS replica may then be used as a mold to fabricate one or more biocompatible MAS.

Fabricating the replica includes, at 314, cleaning the silicon MAS. For example, the silicon MAS is cleaned by immersing the silicon MAS sequentially in the piranha solution ($H_2O_2$:$H_2SO_4$, 1:3), DI water, and ethanol. The cleaned silicon MAS is dried with air at room temperature.

Fabricating the replica includes, at 316, treating the surfaces of the cleaned silicon MAS to prevent the PDMS bonding to the silicon MAS. In some embodiments, the cleaned silicon MAS may be covalently bonded with hexamethyldisilazane (HMDS). For example, the surfaces of the cleaned silicon MAS are bonded with HMDS via chemical vapor deposition in a vacuum chamber. By bonding the HMDS to the surface of the silicon MAS, the PDMS will not bond to the silicon MAS in the following steps.

Fabricating the replica includes, at 318, coating a PDMS layer onto the HMDS bonded silicon MAS from 316 to obtain the PDMS replica. By coating the silicon MAS with the PDMS, all the gaps between the micropillars of the silicon MAS are filled with the PDMS. The thickness of the PDMS layer may be greater than the height of the micropillars of the silicon MAS. In this way, the PDMS indentations are connected with each other and the PDMS replica is a continuous piece of material. Further, the coated PDMS layer is cured or solidified at 318.

In some embodiments, the PDMS mixture may be prepared by mixing silicone elastomer curing agent with silicone elastomer base (SYLGARD® 184 SILICONE ELASTOMER KIT) in a volume ratio of 1:5. The PDMS mixture may be poured onto the silicon MAS and cover the micropillars of the silicon MAS. The PDMS covered silicon MAS may be cured at 65° C. for 45 min to polymerize the PDMS. After polymerization, the PDMS becomes solid and can be peeled off the silicon MAS.

At 320, after the PDMS is fully polymerized, the PDMS replica is removed from the silicon MAS. Since the silicon MAS surface is treated, the PDMS replica may be removed easily from the silicon MAS by peeling or lifting the PDMS replica from the silicon MAS.

FIG. 5 illustrates the process for manufacturing the PDMS replica. Similar to FIG. 4, in FIG. 5, the silicon MAS is positioned in the x-y plane, with the micropillars extending in the z direction. Schematics 501 and 502 of FIG. 5 show the cleaned silicon MAS and the HMDS bonded silicon MAS, respectively.

Schematic 503 of FIG. 5 shows the silicon MAS 505 covered with PDMS 506. The PDMS 506 layer is thicker than the height of the micropillars of the silicon MAS. The PDMS fills the gaps between the micropillars of the silicon MAS, and also covers the top of the silicon MAS. As such, the micropillars of the silicon MAS are fully embedded within the PDMS layer.

Schematic 504 of FIG. 5 shows the PDMS replica peeled off from the silicon MAS, without the silicon MAS. The PDMS replica is a continuous piece of polymerized PDMS. The bottom side 508 of the PDMS replica contains an array of indentations 510 complimentary to the micropillars of the silicon MAS. The indentations do not extend through the entire height of the PDMS replica in the z direction. The top surface 509 of the PDMS replica is a continuous flat surface. As such, the indentations are covered or sealed with PDMS on the top, so that the height of the biocompatible micropillars may be controlled.

Turning back to FIG. 3, at 322, the biocompatible MAS may be fabricated based on the PDMS replica. In some embodiments, the indentations of the PDMS replica may be filled with a biocompatible material. In some embodiments, the indentations of the PDMS replica may be filled by imprinting the PDMS replica on a layer of biocompatible material. For example, the PDMS replica may be pressed into a layer of biocompatible material so that the indentations of the PDMS replica are filled with the biocompatible material. In one example, the PDMS replica may imprint on the biocompatible material layer by applying pressure and heat to the sample. After curing or solidifying the biocompatible material, the PDMS replica may be removed to obtain the biocompatible MAS.

Fabricating the biocompatible MAS includes, at 324, treating the surfaces of the PDMS replica to prevent bonding between the PDMS and the biocompatible material. In some embodiments, the surfaces of the PDMS replica may be coated with HMDS. For example, the PDMS replica may be kept in HMDS vapor for 30 minutes at room temperature.

Fabricating the biocompatible MAS includes, at 326, forming a layer of biocompatible material, such as a biocompatible polymer. The vertical height (or thickness) of the layer may be greater than the height of the micropillars of the silicon MAS. For example, the thickness of the biocompatible polymer layer may be 5-10 μm. The biocompatible polymer may contain an amine group. For example, the biocompatible polymer may be poly lactic-co-glycolic acid (PLGA)-$NH_2$, polystyrene-$NH_2$, or chitosan. In some embodiments, the biocompatible polymer may be coated on a surface of a flat substrate. The substrate may be a glass slide, a petri dish, or deformable films. In some embodiments, the biocompatible polymer may be spin coated onto the substrate. As an example, a solution of PLGA-$NH_2$ is prepared by dissolving PLGA-$NH_2$ (Nanosoft Polymers) in acetonitrile in a 1:10 ratio. A small volume (such as 500 μL) of the solution is smeared on the substrate, then spin coated at 2000 rpm.

Fabricating the biocompatible material includes, at 328, imprinting the PDMS replica from 324 onto the layer of biocompatible material. In some embodiments, the PDMS replica may be imprinted onto the substrate coated with the biocompatible polymer. The imprinting process may include flowing the biocompatible polymer into the indentations of the PDMS replica, so that the indentations are filled with the biocompatible polymer. The biocompatible polymer may then be polymerized.

In some embodiments, the PDMS replica may be directly positioned on top of the biocompatible polymer layer with the side with indentations facing the biocompatible polymer layer. The PDMS replica, together with the biocompatible polymer coated substrate, may be heated under a pressure to flow the biocompatible polymer into the indentations of the PDMS replica. As such, micropillars of the biocompatible polymer are formed on the substrate. The biocompatible polymers may be further polymerized and solidified under the heat and pressure. The temperature and the pressure may be determined based on the type of the biocompatible polymer. For example, if the biocompatible polymer is PLGA-$NH_2$, Polystyrene-$NH_2$, or chitosan, the PDMS replica and the biocompatible polymer coated substrate may be heated at 80-120° C. under the pressure of 50 psi for 1 minute.

At 330, after the biocompatible polymer is polymerized, the PDMS replica may be removed to obtain the biocompatible MAS. In some embodiments, the biocompatible polymer layer with the PDMS replica on top may be cooled down. In one example, the sample may be cooled at room temperature for 5 minutes. The PDMS replica is then removed from the biocompatible polymer layer to obtain the biocompatible MAS.

FIG. 6 illustrates an example process for fabricating the biocompatible MAS using the PDMS replica. The samples in FIG. 6 are positioned in the x-y plane, and the z direction is the vertical direction. Schematic 601 illustrates a flat substrate 604. Schematic 621 illustrates the substrate 604 coated with a layer of biocompatible polymer 605 on one side (such as the top side) of the substrate 604.

Schematic 602 shows the treated PDMS replica 606 positioned on top of the substrate 604 coated with biocompatible polymer 605. After heating, the biocompatible polymer is displaced and flows into the indentations of the PDMS replica 406. When the indentations are completely filled with the biocompatible polymer, multiple micropillars are formed on the side the substrate coated with biocompatible polymer. As such, the PDMS replica serves as a mold for molding the biocompatible polymers into micropillars.

Schematic 603 of FIG. 6 shows the biocompatible MAS after removing the PDMS replica 606. The biocompatible MAS includes substrate 604 and an array of biocompatible micropillars 607 on the top surface 608 of the substrate 604. In some embodiments, the biocompatible micropillars 607 are made from biocompatible polymer, and are in direct contact with the substrate 604. The top surface of the substrate 604 is not coated with the biocompatible polymer. In some embodiments, the biocompatible micropillars 607 are not in direct contact with the substrate 604, but are separated from the substrate 604 with a layer of biocompatible polymer. In some embodiments, the top surface of the substrate 604 is coated with a layer of the biocompatible polymer 608. The thickness of the biocompatible polymer layer may be under 5 m.

The size and the arrangement of the biocompatible micropillars 607 on the top surface 608 is the same as the micropillars of the silicon MAS. For example, the height 609 of each biocompatible micropillars may be less than 10 µm or other suitable height. In one example, the height 609 of the biocompatible micropillar is 5-10 µm. In one example, each micropillar may be cylindrical or cylindrical cone shaped. The diameter 610 of a lateral cross-section of the biocompatible micropillar is less than 2 µm. In one example, the diameter 610 is 0.8-2 µm. The spacing of the biocompatible micropillars is 2 µm or less. In one example, the biocompatible micropillars are 1.0-2.0 µm apart from each other.

Turning back to FIG. 3, in some embodiments, at 332, the biocompatible MAS from 322 may optionally be functionalized to obtain a biocompatible MAS with increased bio-affinity to certain type of target cells. In some embodiments, the biocompatible MAS may be functionalized with antibodies targeting certain type of target cells. The antibodies may be linked to the biocompatible polymer with a linker. For example, biotin may be linked to the amine group of the biocompatible polymer, and the antibody may be linked to the biocompatible polymer via Biotin-Neutravidin interaction.

Functionalizing the biocompatible MAS includes, at 334, introducing biotin functional groups to the surface of the biocompatible MAS. For example, the biocompatible MAS may be immersed in a solution containing NHS-PEG-Biotin. The NHS group reacts with the amine group of the biocompatible polymer, and links biotin to the biocompatible polymer.

FIG. 7 illustrates an example procedure for functionalizing the biocompatible MAS with biotinylated antibodies. NHS-PEG-biotin 702 may be applied to the top surface of the biocompatible MAS 701, causing biotin to be linked with the amine group of the biocompatible polymer. As shown in 703 of FIG. 7, the biotin end of the NHS-PEG-biotin extends away from the biocompatible MAS.

Turning back to FIG. 3, functionalizing the biocompatible MAS includes, at 336, after introducing the biotin, modifying the surface of the biocompatible MAS with a linker. The linker may link the biotin end of the biocompatible MAS with an antibody. In one example, the linker may be neutravidin or streptavidin.

Functionalizing the biocompatible MAS includes, at 338, further linking the surface of the biocompatible MAS with biotinylated antibodies. In one example, the biotinylated antibodies may be linked to biocompatible MAS via Biotin-Neutravidin interaction. The antibodies may be selected based on the target cell type. The antibodies can bind with surface antigens of the target cell.

In this way, the biocompatible MAS may be manufactured within a chemical hood in a regular chemistry lab. The manufacturing process is eco-friendly with minimal influence to the operator or the environment. The size of the micropillars and the arrangement of the micropillars on the biocompatible MAS are in the micron scale, and are tunable. The biocompatible MAS may be reproduced accurately at large quantity. Further, there is less requirement on the substrate of the biocompatible MAS. For example, the substrate may be a deformable film. Moreover, biocompatible micropillars covering a large surface area may be manufactured.

FIG. 8 shows selective adhesion to target cells with the biocompatible MAS 801 functionalized with antibodies 802. A sample 803 containing different types of cells may be passed over the biocompatible MAS. In some embodiments, the sample may be a blood sample that includes red blood cells 804, white blood cells (WBCs) 805, and target cells 806. The target cells 806 may specifically bind to the antibodies present on the biocompatible MAS as shown at 807.

FIG. 9 shows cell attachment efficiencies of the biocompatible MAS compared to other substrates. The x-axis shows the type of substrates. Four types of substrates including biocompatible MAS made with PLGA (PLGA MAS), PLGA coated flat substrate (PLGA Flat), silicon MAS (Si MAS), and flat silicon substrate (Si Flat) were used for evaluation. Each of the substrates (e.g., the PLGAMAS, PLGA flat, Si MAS, and Si Flat) were functionalized with biotinylated anti-EpCAM. The y-axis is the cell attachment efficiency. The cell attachment efficiency ranges from 0 to 100%. Three types of cells including MCF7, A549, and WBCs were prepared. For each type of cell, 20 k cells were suspended in 500 µL RPMI and the cell suspension smeared on each of the four types of substrates. After incubation at 37° C. for 45 minutes, the substrates were washed with PBS, and the cells attached to the substrate were fixed with 4% PFA. After DAPI staining, the number of cells attached to each substrate were counted.

In another embodiment, the number of the attached cells may be calculated based on the number of cells not attached to the substrate after the incubation. Attachment efficiency for each type of the cells may be evaluated by dividing the number of attached cells by the total number of cells incubated with the substrate. For example, to evaluate the cell attachment efficiency of the functionalized PLGA MAS to the MCF7 cells, the MCF7 cells may be incubated with the biocompatible MAS. The attachment efficiency may be calculated by dividing the number of MCF7 cells attached to the biocompatible MAS by the total number of MCF7 cells incubated with the biocompatible MAS.

For the MCF7 and A549 cells, the cell attachment efficiency of the functionalized PLGA MAS is the highest compared to the attachment efficiency of the flat PLGA substrate, silicon MAS, and the flat silicon substrate. The attachment efficiency of the functionalized PLGA MAS is low for the WBCs. This indicates that the functionalized PLGA MAS has high selective cell attachment efficiency to the target cells (such as MCF7 and A549), while the cell attachment efficiency to non-targeted cells (such as WBCs) is low. Moreover, the cell attachment efficiencies of the functionalized PLGA MAS and the silicon MAS to the MCF7 and A549 cells are higher than the cell attachment efficiencies of the flat PLGA substrate and flat silicon substrate to the MCF7 and A549 cells. This indicates that the cell attachment efficiencies are sensitive to the microstructure of the MAS. The three-dimensional pillars in the micron range may enhance cell attachment efficiency.

FIG. 10 shows the cell proliferation rate of cells on different types of substrates. The x-axis is time, and the y-axis is the number of cells detected on the substrates. Four types of substrates including biocompatible MAS made with PLGA (PLGA MAS), PLGA coated flat substrate (PLGA flat), silicon MAS (Si MAS), and flat silicon substrate (Si Flat) were evaluated. Each substrate was functionalized with anti-EPCAM antibodies. In particular, each substrate was incubated with 20 k of MCF7 cells in 2 mL of RPMI culture medium. The number of cells on the substrate was counted over time during the incubation. For example, at different time points, the cells were stained with DIO and counted under the fluorescent microscope.

The number of the cells increases for all four types of substrates over time. The proliferation rate (that is, the rate of cell number increase over time) is lower in the first 24 hours of incubation, compared to the proliferation rate after 24 hours of incubation, for all types of the substrates. The proliferation rate is the highest for the PLGA MAS. Further, the proliferation rate of the substrates with micropillar array (PLGA MAS and Si MAS) are higher than respective the proliferation rates of the flat substrate made with the same material. This indicates that cell proliferation may be sensitive to the micro-environment, and that the three-dimensional pillars in the micron scale may enhance cell proliferation rate. Moreover, the proliferation rates of substrates made from PLGA is higher than the silicon substrates, which indicates that the biocompatible polymer may facilitate cell proliferation.

The technical effect of fabricating the biocompatible MAS based on the PDMS replica made from the silicon MAS includes the MAS contains biocompatible polymer that can facilitate cell attachment and cell proliferation. The technical effect of fabricating the silicon MAS with colloid lithography including eco-friendly wet etching is that the micropillar array covering a large surface area and with micropillars in the micron scale may be accurately fabricated within a chemical hood. Further, the size of the micropillars may be easily adjusted. The technical effect of functionalizing the biocompatible MAS is increasing the cell attachment efficiency of the substrate to the target cells while not affecting the cell attachment efficiency to the non-targeted cells.

As one embodiment, a method for preparing a biocompatible micropillar array substrate (MAS) with multiple micropillars comprises preparing a replica based on a silicon MAS with multiple micropillars, and preparing the biocompatible MAS by imprinting the replica on a layer of biocompatible polymer, where a configuration of the multiple micropillars of the silicon MAS and a configuration of the multiple micropillars of the biocompatible MAS are the same. In a first example of the method, preparing the replica based on the silicon MAS includes treating a surface of the silicon MAS with hexamethyldisilazane (HMDS), and coating the treated surface of the silicon MAS with polydimethylsiloxane (PDMS). A second example of the method optionally includes the first example and further includes, wherein the replica includes a plurality of indentations, and imprinting the replica on the layer of biocompatible polymer includes flowing the biocompatible polymer into the indentations. A third example of the method optionally includes one or more of the first and second examples, and further includes, wherein the biocompatible polymer is flowed into the indentations by applying pressure and heat to the replica and the biocompatible polymer. A fourth example of the method optionally includes one or more of the first through third examples, and further includes, wherein imprinting the replica on the layer of biocompatible polymer further includes polymerizing the biocompatible polymer after flowing the biocompatible polymer into the indentations, and removing the replica from the polymerized biocompatible polymer. A fifth example of the method optionally includes one or more of the first through fourth examples, and further includes, wherein the layer of biocompatible polymer is formed by coating a flat substrate with the biocompatible polymer. A sixth example of the method optionally includes one or more of the first through fifth examples, and further includes, wherein the flat substrate is deformable.

As another embodiment, a method for fabricating a biocompatible micropillar array substrate (MAS) with multiple micropillars, comprises preparing a silicon MAS with multiple micropillars; fabricating a polydimethylsiloxane (PDMS) replica complimentary to the silicon MAS; and fabricating the biocompatible MAS with multiple micropillars of a biocompatible polymer using the PDMS replica, wherein a configuration of the multiple micropillars of the silicon MAS and a configuration of the multiple micropillars of the biocompatible MAS are the same. In a first example of the method, preparing the silicon MAS includes fabricating the silicon MAS with a colloid lithography procedure. A second example of the method optionally includes the first example and further includes, wherein fabricating the silicon MAS with the colloid lithography procedure includes etching a silicon substrate with polystyrene beads dispersed on top of a surface of the silicon substrate. A third example of the method optionally includes one or more of the first and second examples, and further includes, wherein the silicon substrate is etched with $NH_4F$. A fourth example of the method optionally includes one or more of the first through third examples, and further includes, wherein etching the silicon substrate with polystyrene beads dispersed on top of the silicon substrate includes immersing the silicon substrate with polystyrene beads in a first aqueous solution containing $NH_4F$, $AgNO_3$, and $H_2O_2$, and then immersing the silicon substrate in a second aqueous solution containing $NH_4F$ and $H_2O_2$. A fifth example of the method optionally includes one or more of the first through fourth examples, and further includes, wherein the polystyrene beads are from 0.8 to 2 μm in diameter. A sixth example of the method optionally includes one or more of the first through fifth examples, and further includes, wherein the biocompatible polymer includes an amine group. A seventh example of the method optionally includes one or more of the first through sixth examples, and further includes, wherein the biocompatible polymer is poly lactic-co-glycolic acid (PLGA), polystyrene, or chitosan. An eighth example of the method optionally includes one or more of the first through seventh examples, and further includes, wherein fabricating the biocompatible MAS based on the PDMS replica includes imprinting the PDMS replica onto a substrate coated with a layer of the biocompatible polymer, the biocompatible polymer layer with a thickness from 5 to 10 μm.

As another embodiment, a biocompatible micropillar array substrate (MAS), comprises a plurality of micropillars of a biocompatible polymer arranged on a surface of a flat substrate, the plurality of micropillars spaced less than 2 μm from each other and having a height of 5-10 μm, the biocompatible MAS mirrors a silicon MAS with a plurality of micropillars, wherein a configuration of the plurality of micropillars of the silicon MAS and a configuration of the plurality of micropillars of the biocompatible MAS are the same. In a first example of the biocompatible MAS, each of the plurality of micropillars has a cylindrical cone shape, and a diameter at a lateral cross-section of each micropillar is from 0.8 to 2 μm. A second example of the biocompatible MAS optionally includes the first example and further includes, wherein a surface of the biocompatible MAS is linked with a biotinylated antibody via a linker. A third example of the biocompatible MAS optionally includes one or more of the first and second examples, and further includes, wherein the linker is Neutravidin.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for preparing a biocompatible micropillar array substrate (MAS) with multiple micropillars comprising:
preparing a replica based on a silicon MAS with multiple micropillars, the replica is a PDMS replica that has indentations that complement the micropillars, wherein preparing the replica based on the silicon MAS includes treating a surface of the silicon MAS with hexamethyldisilazane (HMDS), and coating the treated surface of the silicon MAS with polydimethylsiloxane (PDMS); and
preparing the biocompatible MAS by imprinting the replica on a layer of biocompatible polymer, where a configuration of the multiple micropillars of the silicon MAS and a configuration of the multiple micropillars of the biocompatible MAS are the same, wherein the multiple micropillars of the biocompatible MAS are spaced less than 10 μm from each other and having a height of 10 μm or less, wherein the layer of biocompatible polymer is formed by coating a flat substrate with the biocompatible polymer, wherein the flat substrate is deformable, wherein the flat substrate is extended in a x-plane, a y-plane, and a z-plane, wherein the height of the micropillar is measured in the z-plane, wherein the micropillar is cylindrical in shape, wherein the biocompatible micropillar array substrate (MAS) are solidified and removed from the replica to obtain the biocompatible MAS, wherein the biocompatible MAS is functionalized with an antibody targeting one or more cell types, wherein the silicon MAS serves as a master mold for molding the replica, wherein the silicon MAS is fabricated with colloid lithography including wet etching a silicon substrate with polystyrene (PS) beads self-assembled on a surface of the silicon substrate, wherein the biocompatible MAS is functionalized to increase a cell attachment efficiency of the silicon substrate to a plurality of target cells while not affecting the cell attachment efficiency to a plurality of non-targeted cells.

2. The method of claim 1, wherein the replica includes a plurality of indentations, and imprinting the replica on the layer of biocompatible polymer includes flowing the biocompatible polymer into the indentations.

3. The method of claim 2,
wherein the indentations are placed on one side of the replica and are sized to be complimentary to the micropillars of the silicon MAS, and the other side of the replica is sealed so that the indentations do not extend through the entire height of the replica,
wherein preparing the biocompatible MAS by imprinting the replica on a layer of biocompatible polymer comprising positioning the replica on top of the biocompatible polymer with the indentations facing down towards the biocompatible polymer and heating the replica together with the biocompatible polymer under a pressure to flow the biocompatible polymer upwards into the indentations of the replica to form micropillars when cooled.

4. The method of claim 2, wherein imprinting the replica on the layer of biocompatible polymer further includes polymerizing the biocompatible polymer after flowing the biocompatible polymer into the indentations, and removing the replica from the polymerized biocompatible polymer.

5. A method for fabricating a biocompatible micropillar array substrate (MAS) with multiple micropillars, comprising:
preparing a silicon MAS with multiple micropillars, wherein preparing the silicon MAS includes fabricating the silicon MAS with a colloid lithography procedure, wherein fabricating the silicon MAS with the colloid lithography procedure includes dispersing polystyrene beads on top of a surface of a silicon substrate and etching exposed areas of the surface of the silicon substrate;
fabricating a polydimethylsiloxane (PDMS) replica complimentary to the silicon MAS;
fabricating the biocompatible MAS with multiple micropillars of a biocompatible polymer using the PDMS replica, wherein a configuration of the multiple micropillars of the silicon MAS and a configuration of the multiple micropillars of the biocompatible MAS are the same, wherein the biocompatible polymer includes an amine group; and
dissolving the polystyrene beads into ethanol to form a single layer and transferring the single layer of the polystyrene beads to a surface of a pre-cleaned silicon wafer, wherein the multiple micropillars of the biocompatible MAS are spaced less than 10 μm from each other and having a height of 10 μm or less, wherein the height of the micropillar is measured in a z-plane, wherein the micropillar is cylindrical in shape, wherein the biocompatible micropillar array substrate (MAS) are solidified and removed from the replica to obtain the biocompatible MAS, wherein the biocompatible MAS is functionalized with an antibody targeting one or more cell types, wherein the silicon MAS serves as a master mold for molding the replica, wherein the silicon substrate covered with polystyrene beads is etched to remove the silicon not covered by the polystyrene beads, wherein the silicon substrate covered with a reduced size of the PS beads is wet etched using $NH_4F$ to remove silicon from the silicon substrate that is not covered with the polystyrene beads.

6. The method of claim 5, wherein etching the exposed areas of the surface of the silicon substrate include etching the exposed areas of the surface with $NH_4F$.

7. The method of claim 5, wherein etching the exposed areas of the surface includes immersing the silicon substrate with the polystyrene beads in a first aqueous solution containing $NH_4F$, $AgNO_3$, and $H_2O_2$, and then immersing the silicon substrate in a second aqueous solution containing $NH_4F$ and $H_2O_2$.

8. The method of claim 5, wherein the polystyrene beads are from 0.8 to 2 μm in diameter.

9. The method of claim 5, wherein the biocompatible polymer is poly lactic-co-glycolic acid (PLGA), polystyrene, or chitosan.

10. The method of claim 5, wherein fabricating the biocompatible MAS based on the PDMS replica includes imprinting the PDMS replica onto a substrate coated with a layer of the biocompatible polymer, the biocompatible polymer layer with a thickness from 5 to 10 μm.

11. A method for preparing a biocompatible micropillar array substrate (MAS) with multiple micropillars, comprising:
preparing a replica based on a silicon MAS with multiple micropillars, wherein preparing the silicon MAS includes fabricating the silicon MAS with a colloid lithography procedure, wherein fabricating the silicon MAS with the colloid lithography procedure includes dispersing polystyrene beads on top of a surface of a silicon substrate and etching exposed areas of the surface of the silicon substrate; and
preparing the biocompatible MAS by imprinting the replica on a layer of biocompatible polymer, where a configuration of the multiple micropillars of the silicon MAS and a configuration of the multiple micropillars of the biocompatible MAS are the same, wherein the multiple micropillars of the biocompatible MAS are spaced less than 10 μm from each other and having a height of 10 μm or less, wherein the layer of biocompatible polymer is formed by coating a flat substrate with the biocompatible polymer, wherein the flat substrate is deformable, wherein the flat substrate is extended in a x-plane, a y-plane, and a z-plane, wherein the height of the micropillar is measured in the z-plane, wherein the micropillar is cylindrical in shape, wherein the biocompatible micropillar array substrate (MAS) are solidified and removed from the replica to obtain the biocompatible MAS, wherein the biocompatible MAS is functionalized with an antibody targeting one or more cell types, wherein the silicon MAS serves as a master mold for molding the replica, wherein the silicon substrate covered with polystyrene beads is etched to remove the silicon not covered by the polystyrene beads, wherein the silicon substrate covered with a reduced size of the PS beads is wet etched using $NH_4F$ to remove silicon from the silicon substrate that is not covered with the polystyrene beads.

12. A method for preparing a biocompatible micropillar array substrate (MAS) with multiple micropillars, comprising:
preparing a replica based on a silicon MAS with multiple micropillars, the replica is a PDMS replica that has indentations that complement the micropillars, wherein preparing the silicon MAS includes fabricating the silicon MAS with a colloid lithography procedure, wherein fabricating the silicon MAS with the colloid lithography procedure includes dispersing polystyrene beads on top of a surface of a silicon substrate and etching exposed areas of the surface of the silicon substrate; and
preparing the biocompatible MAS by imprinting the replica on a layer of biocompatible polymer, where a configuration of the multiple micropillars of the silicon MAS and a configuration of the multiple micropillars of the biocompatible MAS are the same;
wherein the multiple micropillars of the biocompatible MAS are spaced less than 10 μm from each other and having a height of 10 μm or less, wherein the layer of biocompatible polymer is formed by coating a flat substrate with the biocompatible polymer, wherein the flat substrate is deformable, wherein the flat substrate is extended in a x-plane, a y-plane, and a z-plane, wherein the height of the micropillar is measured in the z-plane, wherein the micropillar is cylindrical in shape, wherein the biocompatible micropillar array substrate (MAS) are solidified and removed from the replica to obtain the biocompatible MAS, wherein the biocompatible MAS is functionalized with an antibody targeting one or more cell types, wherein the silicon MAS serves as a master mold for molding the replica, wherein the silicon substrate covered with polystyrene beads is etched to remove the silicon not covered by the polystyrene beads, wherein the silicon substrate covered with a reduced size of the PS beads is wet etched using $NH_4F$ to remove silicon from the silicon substrate that is not covered with the polystyrene beads.

13. The method of claim 12, wherein the biocompatible polymer is selected from the group consisting of PLGA-NH2, Polystyrene-NH2, and chitosan, and wherein preparing the biocompatible MAS by imprinting the replica on a layer of biocompatible polymer, where a configuration of the multiple micropillars of the silicon MAS and a configuration of the multiple micropillars of the biocompatible MAS are the same comprises
heating the biocompatible polymer coated substrate at 80-120'C under the pressure of 50 psi for 1 minute.

* * * * *